United States Patent
van den Broek et al.

[11] 3,972,906
[45] Aug. 3, 1976

[54] NOVEL - 11-SUBSTITUTED STEROIDS OF THE ESTRANE SERIES

[75] Inventors: Albertus Joannes van den Broek; Max Salomon de Winter, both of Oss, Netherlands

[73] Assignee: Akzona Incorporated, Asheville, N.C.

[22] Filed: Apr. 15, 1975

[21] Appl. No.: 568,334

[30] Foreign Application Priority Data
Apr. 26, 1974 Netherlands.................. 7405626

[52] U.S. Cl........................... 260/397.45; 260/397.5
[51] Int. Cl.²............................................ C07J 1/00
[58] Field of Search................. 260/397.5, 397.45

*Primary Examiner*—Elbert L. Roberts
*Attorney, Agent, or Firm*—Francis W. Young; Philip M. Pippenger; Hugo E. Weisberger

[57] ABSTRACT

The present invention relates to novel 11-substituted steroids of the estrane series having the general formula

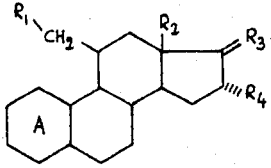

in which
$R_1$ = a free, esterified or etherified hydroxyl group or halogen;
$R_2$ = an alkyl group with 1–4 C-atoms;
$R_3$ = O or ($\alpha$Y)($\beta$Z), in which Y = H or a saturated or unsaturated alkyl group with 1–4 C-atoms and Z = a free, esterified or etherified hydroxyl group;
$R_4$ = H or a free or esterified hydroxyl group; and ring A including carbon atom 6 is

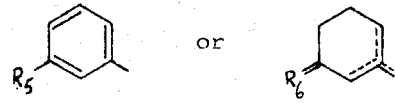

in which
$R_5$ = H or a free, esterified or etherified hydroxyl group,
$R_6$ = $H_2$, O or H($R_7$),
$R_7$ = a free, esterified or etherified hydroxyl group and a double bond is present starting from carbon atom 5, and to processes for their preparation.

The compounds according to the present invention are of value for their contraceptive, estrogenic, progestational, ovulation-inhibiting, gonad-inhibiting and anabolic properties.

8 Claims, No Drawings

NOVEL - 11-SUBSTITUTED STEROIDS OF THE ESTRANE SERIES

The invention relates to novel 11-substituted steroids of the estrane series and to processes for the preparation of these compounds.

Several steroids of the estrane series substituted in the 11-position are known already, for instance the steroids of the estrane series which are substituted in the 11-position by a halogen atom, an oxo-group, a methyl group or a hyroxyl group. These known compounds possess various hormonomimetic or other biological properties. A novel group of 11-substituted steroids of the estrane series with surprisingly strong and valuable properties has now been prepared, to wit steroids of the estrane series which are substituted in the 11-position by a substituted methyl group.

The invention therefore relates to novel 11-substituted steroids of the estrane series of the general formula:

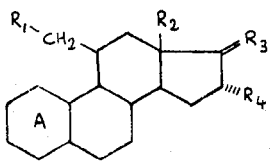

in which
$R_1$ = a free, esterified or etherified hydroxyl group or halogen;
$R_2$ = an alkyl group with 1–4 C-atoms;
$R_3$ = O or ($\alpha$Y) ($\beta$Z), in which Y = H or a saturated or unsaturated alkyl group with 1–4 C-atoms and Z = a free, esterified or etherified hydroxyl group;
$R_4$ = H or a free or esterified hydroxyl group; and ring A including carbon atom 6 is

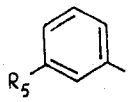

in which
$R_5$ = H or a free, esterified or etherified hydroxyl group, or

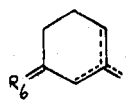

in which
$R_6$ = $H_2$, O or H($R_7$),
$R_7$ = a free, esterified or etherified hydroxyl group, and a double bond is present starting from carbon atom 5.

The invention particularly relates to the group of steroids of the estrane series of the general formula:

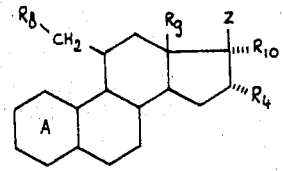

in which
$R_4$ = hydrogen, hydroxy or acyloxy;
$R_8$ = hydroxy, lower alkoxy, lower acyloxy, chloro or fluoro;
$R_9$ = methyl or ethyl;
$R_{10}$ = H or a saturated or unsaturated alkyl group with 1–2 C-atoms, preferably ethynyl;
Z = a free, esterified or etherified hydroxyl group; and ring A is aromatic with a hydroxy-, lower alkoxy- or lower acyloxy group in the 3-position or has the structure

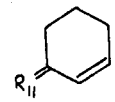

in which
$R_{11}$ = O or $H_2$. -chloromethyl-ethinylestradiol, 11example,

By a lower alkoxy- or acyloxy group is meant an alkoxy- or acyloxy group with 1–8 C-atoms such as, for example, methoxy, ethoxy, cyclopentyloxy, cyclohexenyloxy, acetoxy, pivalyloxy, butyryloxy, oenanthyloxy or hemisuccinyloxy.

The compounds according to the present invention possess very valuble contraceptive, estrogenic, progestational, ovulation-inhibiting, gonad-inhibiting and anabolic properties. In particular the estrogenic properties of the compounds are important, especially of the 11$\beta$-alkoxy-methyl and 11$\beta$-halomethyl compounds, such as, for example, 11$\beta$-methoxymethyl-mestranol, 11$\beta$-methoxymethyl-ethinyl-estradio, 11$\beta$-methoxymethyl-oestriol, 11$\beta$-chloromethyl-ethinylestradio, 11$\beta$-chloromethyl-lynestrenol, 11$\beta$-chloromethyl-norethisterone. The 1$\beta$-alkoxymethyl $\Delta^4$-compounds, such as, for example, 11$\beta$-methoxymethyl-lynestrenol, show moreover a remarkable dissociation of ovulation-inhibiting and progestational activities. The 11$\beta$-substituted-methyl nortestosterone derivatives possess in particular androgenic and anabolic acitivity. Moreover, the 17-oxo compounds according to the invention are important intermediates in the synthesis of therapeutically valuable steroids such as, for exampe, the 17$\alpha$-ethynyl compounds mentioned before.

The compounds according to the invention are of value for use as estrogenic component in contraceptives of the combination type and for use as medicaments in the treatment of estrogen-deficiency-syndromes.

The novel compounds can be prepared by a method known per se by starting from an 11,11-methylene-steroid of the estrane series and reacting this steroid with diborane, whereafter the boron complex thus formed by addition to the exocyclic double bond, is oxidized, for example with hydrogen-peroxide. In this manner a 11$\beta$-hydroxymethyl compound is obtained. The remaining 11$\beta$-substituted-methyl compounds according to the invention can be obtained by esterification, etherification or halogenation of the hydroxy group in the 11-substituent. Before or after this esterification, etherification or halogenation, the substituents elsewhere in the molecule, particularly in the 17-position and in ring A, in so far as not yet present, can be introduced by methods known per se.

In the processes for preparing 11β-substituted-methyl compounds starting from 11,11-methylene compounds, it is preferred to start from an 11,11-methylene steroid of the estrane series having an aromatic A-ring.

The 11,11-methylene steroids to be employed as starting substances can be prepared from the corresponding 11-oxo-steroids in a manner as described in the not-prepublished Dutch patent application No. 7216767.

The novel compounds can also be prepared starting from an 11-oxo-steroid of the estrane series by reacting this steroid with an organo-metal compound with the formula $QCH_2M$, in which Q is an alkoxy group, for example methoxy, and M is lithium or a magnesium halide-radical.

In this case it is preferred to start from an 11-oxo-steroid with an aromatic A-ring. The reaction is performed in an indifferent solvent, for example tetrahydrofuran and preferably at a temperature below −10°C, for example −20°C.

In this manner an alkoxy-methyl group is introduced in the 11-position along with a hydroxy group. By dehydration, for example with thionylchloride/pyridine, the 11-hydroxy group is eliminated, resulting in a $\Delta^{9(11)}$-11-alkoxymethyl compound from which by reduction of the double bond between the carbon atoms 9 and 11, for example with the aid of Pd/C or Pt/C in methanol, and 11β-alkoxymethyl steroid is obtained. By hydrolysis of the alkoxy group, the corresponding 11β-hydroxymethyl compound can be prepared from it, whereafter, if desired, the hydroxy group in the 11-substituent is esterified, re-etherified or halogenated.

Before or after this esterification, etherification or halogenation, the substituents desired in the 17-position and in ring A, in so far as not yet present, can be introduced.

Vulnerable oxy-groups possibly present in the starting substances, for example a hydroxy group in the 3-position, are temporarily protected in the usual way.

When reacting the 11,11-alkylidene steroid with diborane, the diborane can, if desired, be formed in situ, for example from borontrifluoride and a reduction agent, such as $NaBH_4$ or $NaAlH_4$.

The conversion of the hydroxy group in the 11-substituent into a halogen group can be performed in a manner usual for primary hydroxy groups with the aid of a halogenation agent, for example, with a halogenation agent of the general formula:

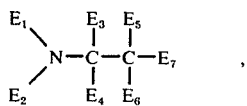

in which $E_1$ and $E_2$ are equal or different alkyl-, aryl- or aralkyl groups or from together with the nitrogen atom a heterocyclic group, $E_3$ and $E_6$ are equal or different halogen atoms, $E_4$ is fluoro, chloro or bromo and $E_5$ is hydrogen or $E_4$ and $E_5$ together form a carbon-carbon bond and $E_7$ is fluoro, chloro or trifluoromethyl, whether or not in the presence of a source of negative halogen-ions, such as lithiumfluoride (fluorination), lithiumchloride (chlorination) or lithiumbromide (bromination), in an inert solvent, for example tetrahydrofuran, and usually at normal temperatures.

Specific examples of the halogenation agent described before are:

for fluorination: N-(2-chloro-1,1,2-trifluoroethyl)-diethylamine;

for chlorination: N-(2-chloro-1,1,2-trifluoroethyl)-diethylamine + LiCl or N-(trichlorovinyl)diethylamine;

for bromination : N-(2-chloro-1,1,2-trifluoroethyl)-diethylamine + LiBr.

Other halogenation agents are N-chloro(bromo)-imides or -amides, such as N-chloro(bromo)-succinimide, -phthalimide or -acetamide, in the presence of anhydrous $SO_2$ or of triphenylphosphine; phosphoropentahalogenides, for example $PCl_5$; chlorine or bromine in the presence of triphenylphosphine or -phosphite; carbontetrachloride or carbontetrabromide in the presence of triphenylphosphine or -phosphite.

As an alternative the hydroxy group in the 11-substituent, after conversion into the mesylate or tosylate, can also be converted into a halogen group with the aid of a halide, for example lithiumfluoride or -chloride in an aprotic solvent, for example dimethylsulphoxide.

Hydroxy groups possibly present in the steroid molecule at other places are temporarily protected against the reaction of the halogenation agent in a manner usual for such groups, for example, by etherification.

After the introduction of an 11-substituent according to the invention, the substituents required in the steroid elsewhere and in so far as not yet present, are introduced by methods known per se.

The substituent required in the 13-position is preferably present already in the starting substance. The 13β-alkyl group may be a methyl, ethyl, propyl, isopropyl, butyl or isobutyl group and is preferably methyl or ethyl.

An aromatic A-ring with a 3-methylether group, if present, can, if desired, be converted into a 3-oxo-$\Delta^4$ group via the Birch-reduction method (reduction with an alkali metal in liquid $NH_3$) and conversion of the $\Delta^{2,5(10)}$-3-enolether by heating with a diluted strong acid. Hydrolysis of the $\Delta^{2,5(10)}$-3-enolether at room temperature with a weak acid, for example acetic acid, yields the 3-oxo-$\Delta^{5(10)}$ compound.

A 3-oxo-$\Delta^4$ group, if present, can, if desired, be converted into a 3β-hydroxy-$\Delta^5$-group by a method known per se, i.e. via a conversion into the $\Delta^{3,5}$-3-enolacylate, a reduction of the double bond between the carbon atoms 3 and 4 and hydrolysis of the $\Delta^5$-3-acylate, after which, if desired, the 3β-hydroxy group is esterified or etherified or split off.

A 3-oxo-$\Delta^4$ group, if present, can, if desired, also be converted into a 3-hydroxy-A-aromatic group, for example microbiologically with the aid of *Arthrobacter simplex*, or chemically, for example, by first converting the 3-oxo-$\Delta^4$ group into the enolacetate, brominating the enolacetate in the 6-position, for example with N-bromo acetamide and treating the bromo derivative with an acid, giving an aromatic A-ring under elimination of HBr.

A 3-oxo- or 3-hydroxy group, if present, can, if desired, be split off for the preparation of the 3-desoxo compounds.

For that purpose the 3-oxo-group is converted into the thioketal group by reaction with a mercaptane or dithiol in the presence of $BF_3$, $ZnCl_2$ or $BF_3$-etherate, whereafter the thioketal group is split off reductively, for example by treatment with an alkali metal, preferably lithium, in the presence of liquid ammonia or a lower aliphatic primary amine, such as methylamine or ethylamine.

A 3-hydroxy group can be eliminated by first converting it into a 3-halo or 3-sulphonyloxy group by halogenation with, for example, phosphorus trichloride or thionylchloride, or sulphonylation with, for example, methane sulphonic acid or toluene sulphonic acid or the acid chloride thereof, whereafter the 3-halo or 3-sulphonyloxy group is split off reductively by treatment with an alkali metal in liquid ammonia, a lower aliphatic amine, such as methylamine, or an alcohol, such as ethanol or by treatment with alkalimetalaluminiumhydride, for example $LiAlH_4$.

For the preparation of 3-desoxo compounds according to the invention it is also possible to start from a 3-des-oxo-11,11-methylene (or 11-oxo) steroid of the estrane series.

The α-hydroxy group, possibly present in 16-position, may already be present in the starting steroid or may be introduced in a compound having already a 11β-substituted-methyl substituent, such as for example 11β-methoxymethyloestrone. In the latter case the 16α-hydroxy group may be introduced by converting a 17-ketone into the $\Delta^{16}$-17-enolacylate, reacting the enolacylate with a peracid so as to obtain the corresponding 16α,17α-epoxy-17-acylate, whereafter the epoxide is opened in alkaline medium to give the 16α-hydroxy-17-ketone.

The substituents desired in the 17-position may already be present in the starting substances. In so far as not yet present they can, if desired, be introduced as yet by a method known per se.

A 17-hydroxy group, if present, can be oxidized to a 17-oxo group, for example by means of the Oppenauer method or with chromium-trioxide. A 17-oxo group, if present, can, if desired, be reduced to a 17-hydroxy group, for example by reduction with $NaBH_4$ in alkaline methanol.

The introduction of a saturated or unsaturated alkyl group in the 17-position is performed by reacting the 17-oxo-steroid with a metal derivative of a saturated or unsaturated, substituted or unsubstituted, aliphatic hydrocarbon, possibly followed by a reduction of the thus introduced side chain. The metal derivative may be a Grignard compound, for example the magnesium bromide of the hydrocarbon in question or an alkyllithium compound.

A special form of performing the condensation reaction for the preparation of the 17β-hydroxy-17α-alkynyl compounds pounds consists therein that the 17-oxo-steroid is reacted with a triple unsaturated hydrocarbon, for example acetylene, in the presence of an alkali metal or an alkali metal compound, such as an alkali metal amide or -alcoholate, or with a metallic compound of a triple unsaturated hydrocarbon, such as an alkali metal- or alkaline earth metal compound, for example potassium acetylide.

The 17-alkylation can also be performed in two phases by preparing in the first phase a 17β-hydroxy-17α-alkynyl compound via a condensation reaction and converting the latter by reduction, for example with hydrogen in the presence of a catalyst, such as nickel or Pd/$BaSO_4$, into the corresponding 17α-alkenyl- or 17β-alkyl compound.

The hydrocarbon radical possibly present in the 17-position of the final products may be, for example, a methyl-, ethyl-, propyl-, butyl-, isopropyl-, vinyl-, propenyl-, isopropenyl-, allyl-, methallyl-, ethynyl-, chloro-ethynyl-, propynyl-, propargyl-, butynyl-, butadienyl-, butadiynyl-, propadienyl- or butenyl-radical.

The ester group possibly present in the 3-, 16- and/or 17-position and/or in the 11-substituent of the final products may be derived from a saturated or unsaturated organic carboxylic acid with 1–18 carbon atoms. The conversion of a hydroxy group into an ester group can be performed by a method known per se, for example by reacting the hydroxy steroid with the acid concerned or a functional derivative thereof, such as the anhydride or the halide. The esterification of the 17β-hydroxy group, formed by the 17-alkylation, can also be performed by having the reaction product of the condensation of the 17-oxo-steroid with a metal derivative of an unsaturated hydrocarbon radical, without preliminary hydrolysis, reacted with the acid in question or a functional derivative thereof. The esterificaton can also be performed, for example, by reacting the steroid with a carboxylic acid anhydride, such as acetic anhydride, in the presence of 4-dimethylaminopyridine, preferably at the same time in the presence os a tertiary amine, such as trimethylamine.

As examples of organic carboxylic acids to be used in the esterification, are mentioned: formic acid, acetic acid, propionic acid, butyric acid, valeric acid, capric acid, undecylic acid, lauric acid, tridecylic acid, myristic acid, pentadecylic acid, oleic acid, palmitic acid, stearic acid, adamantane carboxylic acid, trimethyl acetic acid, diethyl acetic acid, cyclohexane carboxylic acid, cyclopentyl propionic acid, cyclohexyl butyric acid, cyclohexyl propionic acid, undecylenic acid, benzoic acid, phenylacetic acid, phenylpropionic acid, phenylbutyric acid, fumaric acid, malonic acid, succinic acid, glutaric acid, pimelic acid and tartaric acid. As said also functional derivatives thereof can be employed such as the anhydrides or acid chlorides.

The ether groups present in the final products in the 3- and/or 17-positions and/or in the 11-substituent, can be derived from an aliphatic, aromatic, araliphatic or heterocyclic hydrocarbon. Examples of such ether groups are the methylether-, ethylether-, butylether-, cyclopentylether-, tetrahydropyranylether-, cyclohexylether-, and vinylethylether group.

The etherification of a hydroxyl group can be performed according to standard methods. The hydroxy group present, if any, in the 11-substituent can, for example, be converted into the methoxy group with diazomethane in ether or methanol in the presence of fluoroboric acid or $BF_3$-etherate. An alkoxy group can also be formed by reacting the hydroxy group with an alkyl-iodide, for example methyl iodide or ethyl iodide, in the presence of silver oxide or silver carbonate or in the presence of sodium hydride in dimethyl sulphoxide or tetrahydrofuran. A 17β-hydroxy group, for example, may be converted into a 17β-tetrahydropyranyloxy group by reacting a 17β-hydroxy compound with dihydropyran in the presence of p-toluene sulphonic acid in a suitable solvent, such as tetrahydrofuran.

Partial etherification, that is to say, etherification of, for example, the 17β-hydroxy group, whereby there is no desire to etherify the 3-hydroxy group, can be performed by temporarily protecting the hydroxy group that should not be etherified, in a suitable manner. Thus the 17β-hydroxy group in the presence of a 3-hydroxy-A-aromatic-group can be converted into the tetrahydropyranyloxy group by protecting the 3-hydroxy group in the form of the benzoate thereof and removing the benzoate group in the 3-position after the introduction of the ether group in the 17-position.

The compounds obtained according to the process of the invention can, usually subsequent to mixing with auxiliaries and if desired, with other active constituents, be administered in the form of solutions, suspensions, emulsions or solid pharmaceutical shapes such as tablets, pills and coated tablets, parenterally or enterally.

The process according to the invention comprises also the manufacture of preparations with biological activity by incorporating one or more compounds according to the invention into a suitable dosage form. Further the invention in question comprises pharmaceutical shapes containing one or more compounds according to the invention, and medicaments and contraceptives on the basis of one or more compounds according to the invention.

The invention is illustrated with the following examples:

EXAMPLE I a. A mixture of 10 g of 3-hydroxy-11,11-methylene-$\Delta^{1,3,5(10)}$-estratrien-17-one 3-methylether, 100 ml of methylene chloride, 200 ml of ethylene glycol, 30 ml of triethylorthoformate and 0.3 g of p-toluene sulphonic acid was refluxed for 4 hours. The mixture was processed by extraction to obtain a residue of 12.3 g of 3-hydroxy-11,11-methylene-$\Delta^{1,3,5(10)}$-estratrien-17-one 3-methylether 17-ethylene ketal.

b. To a solution of 12.3 g of 3-hydroxy-11,11-methylene-$\Delta^{1,3,5(10)}$-estratrien-17-one 3-methylether 17-ethyleneketal in 390 ml of dry tetrahydrofuran was added in nitrogen atmosphere, 10 ml of a 0.9 molar solution of diborane in tetrahydrofuran whereafter the mixture was stirred for 3 hours at room temperature. Then 260 ml of 10% NaOH were added to the reaction mixture dropwise at 0°C in about 45 minutes and after that 63 ml of 30% $H_2O_2$. The reaction mixture was stirred for another 1.5 hours at 0°C and then for 16 hours at room temperature.

The reaction mixture was poured out into ice water, processed via extraction and crystallisation from diethylether. In this manner 9.1 g of 3-hydroxy-11-$\beta$-hydroxymethyl-$\Delta^{1,3,5(10)}$-estratrien-17-one 3-methylether 17-ethylene ketal were isolated. Melting point: 153°–154°C and $[\alpha]_D$ +123 (chloroform).

c. A solution of 1.7 g of 3-hydroxy-11$\beta$-hydroxymethyl-$\Delta^{1,3,5(10)}$-estratrien-17-one 3-methylether 17-ethylene ketal in 34 ml of acetone was stirred for 2 hours at room temperature with 0.2 ml of concentrated HCl. After pouring out into water, filtering off of the crystals and crystallising from methylene chloridediethylether 1.3 g of 3-hydroxy-11$\beta$-hydroxymethyl-$\Delta^{1,3,5(10)}$-estratrien-17-one 3-methylether were obtained with a melting point of 190°–192°C.

d. In the same way as described in the example I.a. up to and including c., 3-hydroxy-11,11-methylene-18-methyl-$\Delta^{1,3,5(10)}$-estratrien-17-one 3-methylether was converted into 3-hydroxy-11$\beta$-hydroxymethyl-18-methyl-$\Delta^{1,3,5(10)}$estratrien-17-one 3-methylether.

EXAMPLE II a. To 78 ml of dimethyl sulphoxide 3.3 g of NaH were added, whereafter the reaction mixture was heated for 1 hour at 60°–70°C, in a nitrogen atmosphere. Then 1.6 g of 3-hydroxy-11$\beta$-hydroxymethyl-$\Delta^{1,3,5(10)}$-estratrien-17-one 3-methylether 17-ethylene ketal, obtained in example I.b. were added, whereafter the mixture was stirred for one hour at 60°–70°C. After cooling down the reaction mixture to 20°C, 16 ml of methyl iodide were slowly added whereafter the mixture was stirred for 3 hours at room temperature. After processing by pouring out into water and filtering off of the crystals, 1.6 g of 3-hyroxy-11$\beta$-methoxymethyl-$\Delta^{1,3,5(10)}$-estratrien-17-one 3-methylether 17-ethylene ketal were obtained.

b. In the same way as described in example I(c), 1.4 g of 3-hydroxy-11$\beta$-methoxymethyl-$\Delta^{1,3,5(10)}$-estratrien-17-one 3-methylether with a melting point of 171°–172°C and $[\alpha]_D$ +220° (chloroform) were obtained from the ketal obtained in example II(a).

By reduction of this compound with NaBH$_4$ in methanol, 11$\beta$-methoxymethyl-$\Delta^{1,3,5(10)}$-estratrien-3,17$\beta$-diol 3-methylether was obtained from which by esterification of the 17$\beta$-hydroxy-group the 17$\beta$-acylates were prepared, derived from acetic acid, enanthic acid, phenylpropionic acid and undecylenic acid.

c. In an analogous way as described in examples II(a) and (b), 3-hydroxy-11$\beta$-hydroxymethyl-$\Delta^{1,3,5(10)}$-estratrien-17-one 3-methylether 17-ethylene ketal, with the aid of ethyl iodide instead of methyl iodide, was converted into 3-hydroxy-11$\beta$-ethoxymethyl-$\Delta^{1,3,5(10)}$-estratrien-17-one 3-methylether, which by reduction with NaBH$_4$ in methanol yielded the 11$\beta$-ethoxymethyl-$\Delta^{1,3,5(10)}$-estratriene-3,17$\beta$-diol 3-methylether. By esterification of the 17$\beta$-hydroxy group, the 17$\beta$-hemisuccinate of it was prepared.

EXAMPLE III

To a solution of methoxymethyl magnesiumchloride, prepared from 1.9 g of magnesium turnings and 6.6 ml of methoxymethylchloride in 30 ml of tetrahydrofuran at −20°C, a solution of 2 g of 3-hydroxy-$\Delta^{1,3,5(10)}$-estratriene-11,17-dione 3-methylether 17-ethylene ketal in 20 ml of tetrahydrofuran was added at the same temperature.

The reaction mixture was stirred for 8 hours at −20°C whereafter the reaction was stopped with ammonium chloride. After further dilution with water and processing by extraction the crude product was purified by chromatography over silicagel. In this way 1.1 g of 3,11$\beta$-dihydroxy-11$\alpha$-methoxymethyl-$\Delta^{1,3,5(10)}$-estratrien-17-one 3-methylether 17-ethylene ketal were obtained which were dissolved in 10 ml of pyridine and treated with 0.5 ml of thionylchloride at room temperature for 30 minutes.

The reaction mixture was processed by extraction with methylene chloride, washed with diluted HCl to acid, stirred for 30 minutes with diluted HCl and then washed to neutral.

The residue was dissolved in 70 ml of methanol and hydrogenated with 0.3 g of Pd/C (10%) as catalyst.

Separation of the isomer-mixture over a silicagel column and crystallisation gave 0.3 g of 3-hydroxy-11$\beta$-methoxymethyl-$\Delta^{1,3,5(10)}$-estratrien-17-one 3-methylether; melting point: 170°–172°C.

EXAMPLE IV 1 g of 3-hydroxy-11$\beta$-methoxymethyl-$\Delta_{1,3,5(10)}$estratrien-17-one 3-methylether 17-ethylene ketal, obtained in example II(a)., was mixed with 1.5 g of potassium hydroxide and 15 ml of triethylene glycol. The mixture was heated for 5 hours at 200°–210°C under nitrogen. Processing by extraction and evaporation to dryness gave a residue that was dissolved in 20 ml of acetone and treated with 0.1 ml of concentrated HCl at room temperature for 3 hours.

After dilution with water and processing by extraction and crystallisation, pure 3-hydroxy-11β-methoxymethyl-$\Delta^{1,3,5(10)}$-estratrien-17-one was obtained. From this 11β-methoxymethyl-$\Delta^{1,3,5(10)}$-estratriene-3,17β-diol was obtained by reduction with NaBH$_4$ in methanol. After protection of the 3-hydroxy group in the form of the benzoate, the 17β-hydroxy group was etherified, whereafter the 3-benzoate group was hydrolysed to the 3-hydroxy group.

In this manner the 17β-tetrahydropyranylether and the 17β-methoxymethylether were prepared.

EXAMPLE V a. To a potassium acetylide solution in 40 ml of tetrahydrofuran, prepared from 4.6 g of potassium tertiary butoxide and acetylene, 1.3 g of 3-hydroxy-11β-hydroxymethyl-$\Delta^{1,3,5(10)}$-estratrien-17-one 3-methylether were added at 0°–5°C whereafter the reaction mixture was stirred for 4 hours at this temperature.

Processing by extraction, chromatography over silicagel and crystallisation from methylene chloridemethanol gave 1.1 g of 11β-hydroxymethyl-17α-ethynyl-$\Delta^{1,3,5(10)}$-estratriene-3,17β-diol 3-methylether (+ 1 mol crystalmethanol); melting point (100-)151°–152°C and $[\alpha]_D$ +89° (chloroform).

In an analogous manner were prepared from the corresponding 17-oxo-compounds:

11β-methoxymethyl-17α-ethynyl-$\Delta^{1,3,5(10)}$-estratriene-3,17β-diol 3 methylether; melting point 108°–110°C and $[\alpha]_D$ +88° (chloroform);

11β-methoxymethyl-17α-ethynyl-$\Delta^{1,3,5(10)}$-estratriene-3,17β-diol; melting point 207°–209°C and $[\alpha]_D$ +85° (chloroform);

11β-hydroxymethyl-17α-ethynyl-18-methyl-$\Delta^{1,3,5(10)}$-estratriene-3,17β-diol.

Hydrogenation of the 17α-ethynyl-compounds obtained before in a suspension of pre-hydrogenated Pd (5%)/BaSO$_4$ in ethylacetate, yielded the corresponding 17α-vinyl compounds. On further reduction, the corresponding 17α-ethyl compounds were obtained.

b. To a potassium acetylide solution in 30 ml of tetrahydrofuran, prepared from 3.5 g of potassium-t.butoxide and acetylene, 0.9 g of 3-hydroxy-11β-hydroxymethyl-$\Delta^{1,3,5(10)}$-estratriene-17-one were added at 0°–5°C, whereafter the reaction mixture was stirred for 4 hours at 0°–5°C. Then 0.3 ml of acetic anhydride was added to the reaction mixture whereafter the mixture was stirred for 1 hour. Processing of the reaction mixture yielded 0.6 g of 11β-hydroxymethyl-17α-ethynyl-$\Delta^{1,3,5(10)}$-estratriene-3,17β-diol-3-methylether 17β-acetate.

EXAMPLE VI a. A mixture of 35 g of 3-hydroxy-11β-hydroxymethyl-$\Delta^{1,3,5(10)}$-estratrien-17-one 3-methylether 17-ethylene ketal, 600 ml of tetrahydrofuran, 115 ml of dihydropyrane and 1.8 g of p-toluene sulphonic acid was stirred for one hour at room temperature and then processed by extraction with methylene chloride. In this manner an oily residue of 44 g of 3-hydroxy-11β-tetrahydropyranyloxymethyl-$\Delta^{1,3,5(10)}$-estratrien-17-one 3-methylether 17-ethylene ketal were obtained.

b. To a solution of 14 g of lithium in 950 ml of liquid ammonia, a solution of 44 g of 3-hydroxy-11β-tetrahydropyranyloxymethyl-$\Delta^{1,3,5(10)}$-estratrien-17-one 3-methylether 17-ethylene ketal in 560 ml of tetrahydrofuran was added dropwise in 30 minutes at −50°C, whereafter the reaction mixture was stirred for 2 hours at −50°C. After addition of ethanol and evaporation of the ammonia, the residue was processed by extraction. The extract was washed to neutral and evaporated to dryness. The residue obtained was dissolved in 1.5 liter methanol, 378 ml of water and 95 ml of concentrated HCl and refluxed for 20 minutes. After cooling the reaction mixture was evaporated in vacuo to about 1 liter, diluted with water and extracted with methylene chloride. Crystallisation from acetonitril yielded 22 g of 11β-hydroxymethyl-$\Delta^4$-estrene-3,17-dione; melting point 193°–195°C.

c. In a similar manner as described in example VI(a.) and (b.), 3-hydroxy-11β-hydroxymethyl-18-methyl-$\Delta^{1,3,5(10)}$-estratrien-17-one 3-methylether 17-ethylene ketal was converted into 11β-hydroxymethyl-18-methyl-$\Delta^4$-estrene-3,17-dione.

EXAMPLE VII

To a solution of 3.5 g of lithium in 220 ml of liquid ammonia, a solution of 10.0 g of 3-hydroxy-11β-methoxymethyl-$\Delta^{1,3,5(10)}$-estratrien-17-one 3-methylether 17-ethylene ketal in 150 ml of tetrahydrofuran was added at −60°C in 30 minutes. The reaction mixture was stirred for 90 minutes at this temperature whereafter the excess of lithium was inactivated by gently adding 30 ml of ethanol. After evaporation of the ammonia, the reaction mixture was processed by extraction and the residue obtained dissolved in one liter of methanol.

To this solution was added a solution of 12.5 g of oxalic acid 2 aq. in 200 ml of water whereafter the reaction mixture was stirred for three quarters of an hour.

Then the reaction mixture was neutralised with an aqueous sodium bicarbonate solution, processed by extraction and crystallised.

In this manner 5.5 g of pure 11β-methoxymethyl-$\Delta^{5(10)}$-estrene-3,17-dione were obtained.

EXAMPLE VIII

A solution of 10.0 g of 11β-methoxymethyl-$\Delta^4$-estrene-3,17-dione in a mixture of 135 ml of acetic anhydride, 53 ml of acetyl chloride and 5 ml of pyridine was refluxed for 3 hours.

Then the reaction mixture was cooled and diluted with water. The precipitate formed was filtered off. The crystals were dissolved in a mixture of 250 ml of tetrahydrofuran and 250 ml of ethanol and stirred for 3 hours at room temperature with a solution of 22 g of sodiumborohydride in 700 ml of 70% ethanol. The reaction mixture was then diluted with water, extracted with methylene chloride and the extract washed to neutral with water. By crystallisation 6.2 g of pure 11β-methoxymethyl-$\Delta^5$-estrene-3β,17β-diol were obtained.

EXAMPLE IX a. To a suspension of 18 g of 11β-hydroxymethyl-$\Delta^4$-estrene-3,17-dione in 200ml of methanol were successively added at 0°C, 18 ml of ethanedithiol and 18 ml of BF$_3$-etherate. The reaction mixture was stirred for one hour at this temperature, diluted with water and processed by extraction. By crystallisation from acetonitril 15.2 g of 11β-hydroxymethyl-$\Delta^4$-estrene-3,17-dione 3-ethylene dithioketal were obtained; melting point 140°–147°C and $[\alpha]_D$ +164° (chloroform).

b. A solution of 15.2 g of 11β-hydroxymethyl-Δ⁴-estrene-3,17-dione 3-ethylene dithioketal and 0.5 g of p-toluene sulphonic acid in 160 ml of methylene chloride, 320 ml of ethylene glycol and 48 ml of triethylorthoformate was refluxed for 4 hours. Processing by extraction yielded 17 g of 11β-hydroxymethyl-Δ⁴-estrene-3,17-dione 3-ethylene dithioketal 17-ethylene ketal.

c. To a solution of 10.8 g of sodium in 420 ml of liquid ammonia, a solution of 21 g of 11β-hydroxymethyl-Δ⁴-estrene-3,17-dione 3-ethylene dithioketal 17-ethylene ketal was added dropwise in 30 minutes at −40°C, whereafter the mixture was stirred at the same temperature for 30 minutes. After processing and chromatography over silicagel, 14.2 g of 11β-hydroxymethyl-Δ⁴-estren-17-one 17-ethylene ketal were obtained.

d. A solution of 8.8 g of 11β-hydroxymethyl-Δ⁴-estren-17-one 17-ethylene ketal in 175 ml of acetone and 0.9 ml of concentrated HCl was stirred for 1.5 hours at room temperature under $N_2$. Processing by extraction and crystallisation from ether yielded 6.5 g of 11β-hydroxymethyl-Δ⁴-estren-17-one; melting point 123°–125°C and $[\alpha]_D$ +146° (chloroform).

e. In a similar manner as described in example IX(a.) up to and including (d.) 11β-hydroxymethyl-18-methyl-Δ⁴-estrene-3,17-dione was converted into 11β-hydroxymethyl-18-methyl-Δ⁴-estren-17-one.

f. In a similar manner as described in example IX(a.) up to and including (d.), whereby in step c. sodium/ammonia was replaced by lithium/methylamine, 11β-methoxymethyl-Δ⁵⁽¹⁰⁾-estrene-3,17-dione was converted into 11β-methoxymethyl-Δ⁵⁽¹⁰⁾-estren-17-one.

EXAMPLE X

In a similar manner as described in example II, 3.1 g of 11β-hydroxymethyl-Δ⁴-estren-17-one 17-ethylene ketal, as obtained in example IX(c.) were converted into 2.4 g of 11β-methoxymethyl-Δ⁴-estren-17-one; melting point 129°–131°C and $[\alpha]_D^{20}$ +134° (chloroform) and were 2.8 g of 11β-hydroxymethyl-18-methyl-Δ⁴-estren-17-one 17-ethylene ketal converted into 1.9 g of 11β-methoxymethyl-18-methyl-Δ⁴-estren-17-one.

EXAMPLE XI a. To a solution of 2.6 g of 11β-hydroxymethyl-Δ⁴-estren-17-one in 150 ml of tetrahydrofuran 4.4 ml of N-(2-chloro-1,1,2-trifluoroethyl)-diethylamine were added and stirred for 1 hour at room temperature. The reaction mixture was then poured out into a sodium bicarbonate solution and processed by extraction. Chromatography over silicagel and crystallisation from methylene chloride-ether yielded 0.9 g of 11β-fluoromethyl-Δ⁴-estren-17-one.

In a similar manner 11β-hydroxymethyl-18-methyl-Δ⁴-estren-17-one was converted into 11β-fluoromethyl-18-methyl-Δ⁴-estren-17-one.

b. By repeating the process of example XI(a.) in the presence of 3.4 g of lithiumchloride, 11β-chloromethyl-Δ⁴-estren-17-one (melting point 132°–134°C; $[\alpha]_D$ = +139° in $CHCl_3$) was obtained. In a similar manner 11β-chloromethyl-18-methyl-Δ⁴-estren-17-one was obtained from 11β-hydroxymethyl-18-methyl-Δ⁴-estren-17-one.

EXAMPLE XII

To a potassium acetylide solution, prepared from 5,8 g of potassium tertiary-butoxide and acetylene in 50 ml of tetrahydrofuran, 2 g of 11β-methoxymethyl-Δ⁴-estren-17-one were added at 0°C whereafter the mixture was stirred for 2 hours at this temperature.

Processing by extraction and crystallisation from diisopropylether yielded 1.6 g of 11β-methoxymethyl-17α-ethynyl-Δ⁴-estren-17β-ol; melting point 86–88°C and $[\alpha]_D$ +20° (chloroform).

In an analogous manner were obtained from the corresponding 17-oxo-derivatives:

11β-hydroxymethyl-17α-ethynyl-Δ⁴-estren-17β-ol; 11β-chloromethyl-17α-ethynyl-Δ⁴-estren-17β-ol; 11β-fluoromethyl-17α-ethynyl-Δ⁴-estren-17β-ol; 11β-hydroxymethyl-17α-ethynyl-18-methyl-Δ⁴-estren-17β-ol; 11β-chloromethyl-17α-ethynyl-18-methyl-Δ⁴-estren-17β-ol; 11β-fluoromethyl-17α-ethynyl-18-methyl-Δ⁴-estren-17β-ol; 11β-methoxymethyl-17α-ethynyl-18-methyl-Δ⁴-estren-17β-ol.

By esterification of the 17β-hydroxy group of the 11β-chloromethyl-, 11β-fluoromethyl- and 11β-methoxymethyl- compounds obtained in this example, the acetic acid and phenylpropionic acid 17β-esters of these compounds were prepared.

By etherification of the 17β-hydroxy group of the 11β-methoxymethyl-17α-ethynyl compounds obtained above, the 17β-methyl-, 17β-vinylethyl- and 17β-tetrahydropyranylether were obtained.

EXAMPLE XIII

A solution of 1 g of 11β-hydroxymethyl-17α-ethynyl-Δ⁴-estren-17β-ol in 2 ml of pyridine and 1 ml of acetic acid anhydride was left to stand for 16 hours at room temperature. Processing by extraction and chromatography over silicagel yielded 1.1 g pure fractions of oily 11β-acetoxymethyl-17α-ethynyl-Δ⁴-estren-17β-ol with $[\alpha]_D$ +23 ° (chloroform).

In an analogous manner 11β-hydroxymethyl-17α-ethynyl-18-methyl-Δ⁴-estren-17β-ol was converted into 11β-acetoxymethyl-17α-ethynyl-18-methyl-Δ⁴-estren-17β-ol.

By using phenylpropionylchloride or pivalylchloride as the case may be instead of acetic acid anhydride, 11β-phenylpropionyloxymethyl-17α-ethynyl-Δ⁴-estren-17β-ol or 11β-pivalyloxymethyl-17α-ethynyl-Δ⁴-estren-17β-ol as the case may be and the corresponding 18-methyl compounds were obtained in a similar manner.

EXAMPLE XIV

A solution of 4 g of 3-hydroxy-11β-methoxymethyl-Δ¹,³,⁵⁽¹⁰⁾-estratrien-17-one 3-methylether 17-ethylene ketal in 60 ml of tetrahydrofuran was added to a solution of 1.5 g of lithium in 100 ml of liquid ammonia at −50°C. The reaction mixture was stirred for 2 hours at this temperature.

After processing by extraction the residue obtained was dissolved in 150 ml of methanol, 40 ml of water and 9.5 ml of concentrated HCl and refluxed for 20 minutes.

Dilution with water, extraction with methylene chloride and crystallisation yielded the pure 11β-methoxymethyl-Δ⁴-estrene-3,17-dione.

EXAMPLE XV

A solution of 0.9 g of 11β-methoxymethyl-Δ⁴-estren-17-one in 15 ml of tetrahydrofuran was added to an allylmagnesium-bromide solution in ether. After stirring for 2 hours at room temperature the reaction mixture was poured into ice water that had been acidified with sulphuric acid. Processing by extraction and crystallisation yielded 0.7 g of 11β-methoxymethyl-17α-allyl-Δ⁴-estren-17β-ol. By substituting the allylmagnesium bromide solution in the process described before by a methyllithium solution, 11β-methoxymethyl-17α-methyl-Δ⁴-estren-17β-ol was obtained.

EXAMPLE XVI

A mixture of 2 g of 11β-methoxymethyl-Δ⁴-estrene-3,17-dione, 10 ml of methanol and 1 ml of pyrrolidine was boiled for 15 minutes. After cooling down to 0°C the precipitate formed was filtered off and washed with cold methanol. In this manner 2.1 g of 3-N-pyrrolidinyl-11β-methoxymethyl-Δ³,⁵-estradien-17-one were obtained which were added to a potassium acetylide solution, prepared by bubbling acetylene through a suspension of 3.1 g of potassium-t-butoxyde in 100 ml of tetrahydrofuran.

After stirring for 45 minutes at 0°–5°C, the reaction mixture was poured out into water, filtered off and added to an acetic acid-water-methanol-sodium acetate mixture for the elimination of the 3-pyrrolidino group.

After processing by filtration, chromatography over silicagel and crystallisation 1.4 g of 11β-methoxymethyl-17α-ethynyl-17β-hydroxy-Δ⁴-estren-3-one were obtained.

By substituting the potassium acetylide solution in the process described before by a sodiumvinyl acetylide solution which was obtained by reaction of vinyl acetylene with sodium amide in liquid ammonia, 11β-methoxymethyl-17α-but-1-yn-3-enyl- ⁴-estren-17β-ol was prepared in a similar manner.

EXAMPLE XVII a. A mixture of 6 g of 3-hydroxy-11β-methoxymethyl-Δ¹,³,⁵⁽¹⁰⁾-estratrien-17-one, as obtained in Example IV, and 120 ml of distilled isopropenylacetate were stirred at room temperature. After adding 0.9 g of p-toluene sulphonic acid the reaction mixture was heated at about 70°C while slowly distilling off a mixture of acetone and isopropenylacetate. After 3 hours once more 60 ml of isopropenylacetate and 0.45 g of p-toluene sulphonic acid were added and distilling was continued for another three hours. The reaction mixture was cooled to room temperature and 2 g of sodium acetate were added. After evaporation in vacuo the residue was chromatographed on neutral silicagel using toluene/ethylacetate 9:1, yielding 3 g 11β-methoxymethyl-Δ¹,³,⁵⁽¹⁰⁾,¹⁶-estratetraene-3,17-diol 3,17-diacetate.

b. A solution of 3 g 11β-methoxymethyl-Δ¹,³,⁵⁽¹⁰⁾,¹⁶-estratetraene-3,17-diol 3,17-diacetate in 30 ml of dry ether was cooled at 10°C. To this cooled solution a solution of 3.88 g of m-chloro-perbenzoic acid in 30 ml of dry ether was added. The reaction mixture was stirred at room temperature for 30 minutes, then successively washed with water, ice-cold 2N sodium hydroxide solution and water again, until neutral. Evaporation in vacuo gave a residue containing 11β-methoxymethyl-16α,17α-epoxy-Δ¹,³,⁵⁽¹⁰⁾-estratriene-3,17β-diol 3,17β-diacetate, which was dissolved in 60 ml of methanol in a nitrogen atmosphere. 2.4 g of sodiumhydroxide dissolved in 5 ml of water and 30 ml of methanol were added. The temperature raised to 30°C. After cooling and stirring at room temperature for 10 minutes, the solution was cooled to −10°C and 0.6 g of sodiumborohydride were added. The reaction mixture was stirred at −10°C for 6 hours after which the reaction mixture was heated to 30°C and kept at this temperature for half an hour. The reaction was stopped with 50% acetic acid, whereafter methanol was distilled off in vacuo. The residue was stirred with 150 ml of acetone and 20 mg of p-toluene sulphonic acid for 1 hours at room temperature, whereafter the mixture was evaporated to dryness. The residue was crystallised twice from ether, yielding 0.77 g of 11β-methoxymethyl-Δ¹,³,⁵⁽¹⁰⁾-estratriene-3,16α,17β-triol, melting point >230°C, $[\alpha]_D = +136°$ (in chloroform).

c. The 3,16α,17β-triol, obtained in Example XVII(b.), was converted into the 16α,17β-di-hemisuccinate thereof by reacting the triol with succinic acid anhydride in pyridine at 85°C for 5 hours, pouring the reaction mixture into water, extracting the aqueous solution with ether, washing the ether solution with diluted acid and water until neutral, evaporating the ether and crystallizing the residue from a mixture of methanol and water.

EXAMPLE XVIII 20 g of 11β-methoxymethyl-Δ¹,³,⁵⁽¹⁰⁾-estratriene-3,17β-diol 3-methylether (as obtained in Example II(b.)) were dissolved in 300 ml tetrahydrofuran. The solution obtained was added to 1100 ml of liquid ammonia. 10.8 g of chopped lithium wire were added to the stirred solution and the reaction mixture was kept for 2 hours at −35°C. Then the excess of lithium was decomposed by careful addition of about 400 ml of ethanol. The ammonia was evaporated by stirring the mixture overnight at room temperature. The reaction mixture was poured into 7.5 l of cold water. The precipitate was sucked off and washed with water to neutral giving a residue of 19.3 g of crude 11β-methoxymethyl-Δ²,⁵⁽¹⁰⁾-estradiene-3,17β-diol 3-methylether.

This residue was dissolved in 550 ml of methanol. 190 g of a 2N HCl-solution were added to the hot solution. After refluxing for one hour and a half, the reaction mixture was cooled and poured into 3.5 l of cold water. The aqueous mixture was extracted three times with methylene dichloride. The extracts were washed with water to neutral and dried over anhydrous sodiumsulphate. Evaporation of the solution to dryness yielded 20 g of crude 11β-metoxymethyl-17β-hydroxy-Δ⁴-estren-3-one.

After chromatography over 1200 g of silicagel and elution with toluene/ethylacetate 60/40 6.7 g of pure 11β-methoxymethyl-17β-hydroxy-Δ⁴-estren-3-one were obtained as an oil. $E_{mol}^{241\ m\mu} = 15,700$.

EXAMPLE XIX

Under a nitrogen atmosphere a solution of 1.9 ml of decanoylchloride in 7.6 ml of dry benzene was added to a stirred solution of 1.5 g of 11β-methoxymethyl-17β-hydroxy-Δ⁴-estren-3-one in 6 ml of dry pyridine while keeping the temperature at −10°C.

The mixture was stirred overnight (16 hours) at 3°C. After addition of 3.4 ml of pyridine and 6.8 ml of distilled water, stirring was continued for one hour at 0°C and then for 2 hours at 45°C. The reaction mixture was poured into 170 ml of cold water and then extracted 3 times with diethylether.

The extracts were washed 5 times with diluted sulphuric acid and 4 times with a 1.5% sodiumhydroxide solution. The combined extracts were dried over anhydrous sodiumsulphate. Evaporation of the resulting solution to dryness yielded 2.24 g of crude ester.

15

Crystallization from diethylether yielded 0.8 g of pure 11β-methoxymethyl-17β-hydroxy-Δ⁴-estren-3-one 17β-decanoate. Melting point 38°–40°C.

EXAMPLE XX

Under a nitrogen atmosphere 8.1 ml of dihydropyran and 61.5 mg of p-toluene sulphonic acid were added to a stirred solution of 2 g of 11β-methoxymethyl-17β-hydroxy-Δ⁴-estren-3-one in 44 ml of dry tetrahydrofuran.

After stirring for 5 hours at room temperature the reaction mixture was poured into 500 ml of cold water.

Extraction with methylene dichloride and evaporation yielded a residue, which was chromatographed on 300 g of silicagel.

Elution with toluene-ethylacetate (60/40) gave 2.1 g of 11β-methoxymethyl-17β-hydroxy-Δ⁴-estren-3one 17β-tetrahydropyranylether as an oil.

EXAMPLE XXI

To a solution of 4.3 g of N-chlorosuccinimide in 150 ml of dry tetrahydrofuran was successively added a solution of 8.4 g of triphenylphosphine in 90 ml of dry tetrahydrofuran and 3 g of 11β-hydroxymethyl-Δ⁴-estrene-3,17-dione (as obtained in Example VI). After stirring for 2 hours at room temperature, processing by extraction, purification by chromatography and crystallisation from methanol 2.2 g of 11β-chloromethyl-Δ⁴-estrene-3,17-dione were obtained. Melting point 162°–164°C; [α]$_D$ = +14° (chloroform).

In an analogous way as described in Example XVI 2.2 g of 11β-chloromethyl-Δ⁴-estrene-3,17-dione were converted into 1.5 g of 11β-chloromethyl-17α-ethinyl-17β-hydroxy-Δ⁴-estren-3-one. Melting point 213°–214°C; [α]$_D$ = +12° (chloroform).

EXAMPLE XXII 6.8 g of 3-hydroxy-11β-hydroxymethyl-Δ$^{1,3,5(10)}$-estratrien-17-one 3-methylether 17-ethylene ketal were converted into 5.5 g of 3-hydroxy-11β-hydroxymethyl-Δ$^{1,3,5(10)}$-estratrien-17-one according to the method described in Example IV.

5.5 g of 3-hydroxy-11β-hydroxymethyl-Δ$^{1,3,5(10)}$-estratrien-17-one were converted into crude 3-hydroxy-11β-chloromethyl-Δ$^{1,3,5(10)}$-estratriene-17-one according to the method described in Example XXI. This crude product was acetylated to the corresponding 3-acetoxy compound with the aid of acetic acid anhydride in pyridine. Chromatography on silicagel yielded 2.4 g of pure 3-acetoxy-11β-chloromethyl-Δ$^{1,3,5(10)}$-estratrien-17-one. In an analogous way as described in Example V the latter compound was converted into 1.5 g 11β-chloromethyl-17α-ethinyl-Δ$^{1,3,5(10)}$-estratriene-3,17β-diol. Melting point 180°–181°C; [α]$_D$ = +54° (acetone).

We claim:
1. 11β-Methoxymethyl-17α-ethinyl-Δ$^{1,3,5(10)}$-estratriene-3,17β-diol.
2. 11β-Methoxymethyl-Δ$^{1,3,5(10)}$-estratriene-3,16α,17β-triol.
3. 11β-methoxymethyl-17α-ethinyl-Δ⁴-estren-17β-ol.
4. 11β-Chloromethyl-17α-ethinyl-Δ$^{1,3,5(10)}$-estratriene-3,17β-diol.
5. 11β-Chloromethyl-17α-ethinyl-Δ⁴-estren-17β-ol.
6. 11β-Chloromethyl-17α-ethinyl-17β-hydroxy-Δ⁴-estren-3-one.
7. An 11-substituted steroid of the estrane series having the formula:

16

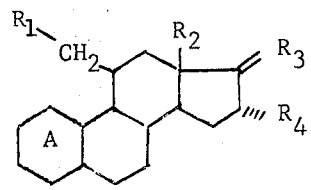

in which
R$_1$ is a member of the group consisting of hydroxy, acyloxy derived from a saturated or unsaturated organic carboxylic acid containing 1 to 18 carbon atoms, alkoxy containing 1 to 6 carbon atoms, cycloalkyloxy containing 5 to 6 carbon atoms, tetrahydropyranyloxy, fluoro and chloro;

R$_2$ is a member of the group consisting of methyl and ethyl;

R$_3$ is O or (αY)(βZ), in which Y = H or a saturated or unsaturated alkyl group containing 1 to 4 carbon atoms and Z = a member of the group consisting of hydroxy, acyloxy derived from a saturated or unsaturated organic carboxylic acid containing 1 to 18 carbon atoms, alkoxy containing 1 to 4 carbon atoms, cycloalkyloxy containing 5 to 6 carbon atoms and tetrahydropyranyloxy;

R$_4$ is a member of the group consisting of hydrogen, hydroxy, and acyloxy derived from a saturated or unsaturated organic carboxylic acid containing 1 to 18 carbon atoms; and ring A including carbon atom 6 is

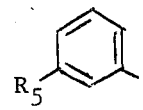

in which
R$_5$ is a member of the group consisting of hydrogen, hydroxy, acyloxy derived from a saturated or unsaturated organic carboxylic acid containing 1 to 18 carbon atoms, alkoxy containing 1 to 4 carbon atoms, cycloalkyloxy containing 5 to 6 carbon atoms, and tetrahydropyranyloxy, or

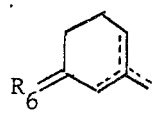

in which
R$_6$ is hydrogen or O and a double bond is present starting from carbon atoms 5.

8. An 11-substituted steroid of the estrane series according to claim 7, in which
R$_1$ is a member of the group consisting of hydroxy, lower acyloxy containing from 1 to 8 carbon atoms, lower alkoxy containing from 1 to 8 carbon atoms, chloro and fluoro;

R$_3$ = (αR$_{10}$)(βZ), wherein R$_{10}$ is a member of the group consisting of hydrogen and a saturated or unsaturated alkyl group containing 1 to 2 carbon atoms;

ring A has the structure

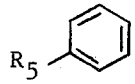 or 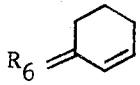

wherein
R$_5$ is a member of the group consisting of hydroxy, lower acyloxy containing 1 to 8 carbon atoms, and lower alkoxy containing 1 to 8 carbon atoms; and R$_2$, R$_4$, R$_6$ and Z have the meanings indicated on claim 7.

* * * * *